(12) United States Patent
Shan et al.

(10) Patent No.: US 9,098,901 B2
(45) Date of Patent: Aug. 4, 2015

(54) DEVICE AND METHOD FOR PROCESSING DATA DERIVABLE FROM REMOTELY DETECTED ELECTROMAGNETIC RADIATION

(71) Applicant: KONINKLIJKE PHILIPS N.V., Eindhoven (NL)

(72) Inventors: Caifeng Shan, Eindhoven (NL); Ihor Olehovych Kirenko, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/029,873

(22) Filed: Sep. 18, 2013

(65) Prior Publication Data

US 2014/0086462 A1 Mar. 27, 2014

Related U.S. Application Data

(60) Provisional application No. 61/703,828, filed on Sep. 21, 2012.

(30) Foreign Application Priority Data

Sep. 21, 2012 (EP) .................................... 12185452

(51) Int. Cl.
*G06K 9/00* (2006.01)
*G06T 7/00* (2006.01)
(Continued)

(52) U.S. Cl.
CPC ............. *G06T 7/0012* (2013.01); *A61B 5/0077* (2013.01); *G06K 9/00362* (2013.01); *A61B 5/1032* (2013.01); *A61B 5/7203* (2013.01); *A61B 2576/02* (2013.01)

(58) Field of Classification Search
None
See application file for complete search history.

(56) References Cited

U.S. PATENT DOCUMENTS 7,972,266 B2 7/2011 Gobeyn et al.
8,062,220 B2 11/2011 Kurtz et al.
(Continued)

FOREIGN PATENT DOCUMENTS

WO 2010100594 A2 9/2010
WO 2011021128 A2 2/2011
WO 2011042858 A1 4/2011

OTHER PUBLICATIONS

Kakumanu, P., et al.; A survey of skin-color modeling and detection methods; 2007; Pattern Recognition; 40:1106-1122.
Verkruysse, W., et al.; Remote plethysmographic imaging using ambient light; 2008; Opt Express; 16(26) 21434-21445.
(Continued)

*Primary Examiner* — Siamak Harandi

(57) ABSTRACT

A device and a method process data derivable from remotely detected electromagnetic radiation emitted or reflected by a subject, which data includes physiological information. An input signal is received and indicative entities thereof are transmitted. The indicative entities are indicative of physiological information representative of at least one vital parameter in a subject of interest. The indicative entities are detected under consideration of at least one defined descriptive model describing a relation between physical skin appearance characteristics and a corresponding representation in the input signal such that non-indicative side information represented by non-indicative entities in the input signal is substantially undetectable in a resulting transmitted signal. The at least one vital parameter is detected from the transmitted signal including the indicative entities under consideration of detected skin color properties representing circulatory activity.

19 Claims, 5 Drawing Sheets

(51) Int. Cl.
*A61B 5/00* (2006.01)
*A61B 5/103* (2006.01)

(56) References Cited

U.S. PATENT DOCUMENTS

| | | | |
|---|---|---|---|
| 8,805,019 B2 | 8/2014 | Jeanne et al. | |
| 2008/0294018 A1 | 11/2008 | Kurtz et al. | |
| 2009/0226071 A1* | 9/2009 | Schuler et al. | 382/133 |
| 2009/0306484 A1* | 12/2009 | Kurtz et al. | 600/300 |
| 2010/0309300 A1* | 12/2010 | Chhibber et al. | 348/77 |

OTHER PUBLICATIONS

Vezhnevets, V., et al.; A Survey on Pixel-Based Skin Color Detection Techniques; 2003; GRAPHICON03, pp. 85-92.

Martinkauppi, B., et al.; Detection of Skin Color under Changing Illumination: A Comparative Study; 2003; Proceedings of Conf. on Image Analysis and Processing; pp. 652-657.

Sahindrakar, P.; Improving Motion Robustness of Contact-less Monitoring of Heart Rate Using Video Analysis; 2011; Technische Universiteit Eindhoven; pp. 1-58. http://alexandria.tue.nl/extral/afstversl/wsk-i/sahindrakar2011.pdf.

* cited by examiner

DEVICE AND METHOD FOR PROCESSING DATA DERIVABLE FROM REMOTELY DETECTED ELECTROMAGNETIC RADIATION

CROSS REFERENCE TO RELATED APPLICATIONS

This application claims the benefit of U.S. provisional application Ser. No. 61/703,828 filed Sep. 21, 2012 and EP provisional application serial no. 12185452.5 filed Sep. 21, 2012, both of which are incorporated herein by reference.

FIELD OF THE INVENTION

The present disclosure relates to a device and method for processing data derivable from remotely detected electromagnetic radiation emitted or reflected by a subject, wherein the data comprises physiological information. More specifically, the present disclosure relates to image processing devices and methods for detecting and monitoring vital parameters in a subject of interest. More particularly, but likewise non-restricting, the present disclosure may further relate to photoplethysmographic and, even more specifically, to remote photoplethysmography approaches. The present disclosure further relates to a computer readable non-transitory medium.

BACKGROUND OF THE INVENTION

WO 2011/021128 A2 (US 2012/0141000) discloses a method and a system for image analysis, including:
obtaining a sequence of images;
performing a vision-based analysis on at least one of the sequence of images to obtain data for classifying a state of a subject represented in the images;
determining at least one value of a physiological parameter of a living being represented in at least one of the sequence of images, wherein the at least one value of the physiological parameter is determined through analysis of image data from the same sequence of images from which the at least one image on which the vision-based analysis is performed is taken; and
classifying a state of the subject using the data obtained with the vision-based analysis and the at least one value of the physiological parameter.
The document further discloses several refinements of the method and the system. For instance, the use of remote photoplethysmographic (PPG) analyses is envisaged.

Basically, photoplethysmography and related vision-based imaging approaches are considered as conventional techniques which can be used to detect physiological information and, based thereon, vital signals or parameters in a subject of interest. Typically, the vital parameters are derived in a mediate way. Vital parameter detection can be based on the detection of volume changes of organs or organ components in a living being (or: subject of interest). More specifically, in some cases, photoplethysmography can be considered as an optical technique which can be utilized to detect blood volume changes in the microvascular portion of the subject's tissue. Typically, photoplethysmographic measurements are directed at the skin surface of the subject. Conventionally known PPG approaches include so-called contact PPG devices which can be attached to the skin of the subject, for instance to a finger tip. Generally, the detected PPG signal (or: waveform) typically comprises a pulsatile physiological waveform attributable to cardiac synchronous changes in the blood volume with every heartbeat. Besides this, the PPG waveform can comprise further physiological information attributable to respiration, oxygen saturation, Traube-Mayer-Hering waves, and even to further physiological phenomena.

Recently, so-called remote photoplethysmography has made enormous progress in that unobtrusive non-contact remote measurements based on conventional cameras have been demonstrated. The term "conventional camera" may refer to off-the-shelf cameras, for instance digital video cameras, digital (photo) cameras providing video recording functionality, or even to integrated cameras in desktop computers, mobile computers, tablets and further mobile devices, such as smartphones. Furthermore, so-called webcams attachable to computing devices may be covered by the term "conventional camera". Furthermore, also medical monitoring devices, video conferencing systems and security surveillance devices can make use of standard camera modules.

Typically, these cameras can comprise responsivity (or: sensitivity) characteristics adapted to the visible portion of the electromagnetic spectrum. As used herein, visible radiation may be defined by the general radiation perception ability of the human eye. By contrast, non-visible radiation may refer to spectral portions which are not visible to a human's eye, unless optical aid devices converting non-visible radiation into visible radiation are utilized. Non-visible radiation may relate to infrared radiation (or: near-infrared radiation) and to ultraviolet (UV) radiation. It should be understood that in some cases, conventional cameras may also be sensitive to non-visible radiation. For instance, a camera's responsivity range may cover the whole visible spectrum and also adjacent spectral portions belonging to the non-visible spectrum or, at least, to a transition area between the visible and the non-visible spectrum. Still, however, exemplarily referring to night vision applications and thermal imaging applications, also cameras primarily directed at non-visible portions of the electromagnetic spectrum can be envisaged.

Nowadays, digital technology gains even further significance in everyday life. By way of example, images and sequences thereof are digitally recorded, processed and reproduced, and can be duplicated without loss. An individual may be confronted with digital imaging devices in public (e.g., traffic monitoring, security monitoring, etc.), in private life (e.g., mobile phones, mobile computing devices including cameras), when doing sports or work-outs (e.g., heart rate monitoring, respiration monitoring applying remote PPG techniques), at work (e.g., vision-based machine or engine monitoring, fatigue monitoring or drowsiness monitoring, vision-based access control, etc.), and even in healthcare environments (e.g., patient monitoring, sleep monitoring, etc.). Consequently, regardless of whether the individual is aware or unaware of being monitored in the individual case, a huge amount of (image) data can be gathered in everyday life.

It is an object of the present invention to provide a system and a method for processing data addressing the above-mentioned issues and enhancing privacy preservation while still allowing for an extraction of vital signals from the recorded data. Furthermore, it would be advantageous to provide a system and a corresponding method configured for hiding privacy related information which is not necessarily essential to the vital signal extraction. It would be further desirable to provide a computer program configured for implementing said method.

In a first aspect of the present disclosure a device for processing data derivable from remotely detected electromagnetic radiation emitted or reflected by a subject is presented, the data comprising physiological information, the device comprising:

a signal detector unit configured for receiving an input signal and for transmitting indicative entities thereof, the indicative entities being indicative of physiological information representative of at least one vital parameter in a subject of interest; and a processing unit configured for extracting the at least one vital parameter from a transmitted signal comprising the indicative entities, wherein the at least one vital parameter is extracted under consideration of detected skin-colored properties representing circulatory activity;

wherein the signal detector unit is further configured for detecting the indicative entities under consideration of at least one defined descriptive model describing a relation between physical skin appearance characteristics and a corresponding representation in the input signal such that non-indicative side information represented by non-indicative entities in the input signal is substantially undetectable in the resulting transmitted signal.

The present disclosure addresses privacy preservation issues by treating non-indicative entities in the input signal in such a way that substantially no conclusions regarding personal or privacy information can be drawn therefrom. It is acknowledged in this connection that the indicative signal entities indeed may also comprise privacy-related information. However, the indicative entities are considered essential for the vital parameter extraction the device is targeted at. Basically, the indicative entities may represent skin portions of the subject of interest. It is worth mentioning in this connection that also a plurality of subjects can be present in or represented by the input signal. Consequently, also the indicative entities may be representative of the plurality of subjects.

The non-indicative entities may cover surroundings or environmental information. The non-indicative entities may further comprise non-indicative information (in terms of the at least one vital parameter of interest) which is still closely related to the observed subject's privacy. This may involve clothing information and housing information. Consequently, also the so-called non-indicative side information can comprise privacy information. By way of example, the non-indicative side information may indicate an individual's personal wealth status. Furthermore, a usual place of residence or a current whereabout might be extracted from the non-indicative side information. It is therefore considered beneficial that the non-indicative entities are substantially disregarded during further processing.

It is understood that also the indicative entities in the input signal may comprise personal or privacy information. Still, given that signal portions formed by the indicative entities can basically be taken out of the overall context or representation observed by the signal detector unit, privacy preservation can be improved. By way of example, primarily indicative skin portions of the subject of interest can remain in the resulting transmitted signal. Assuming that clothing information, housing information and further side information representative of surroundings are no longer detectable in the resulting transmitted signal, the risk of privacy information losses or even privacy information misuse can be reduced significantly.

As used herein, in some embodiments, the term "circulatory activity" may refer to cardiovascular activity or, in general, to vascular activity. It should be understood that also respiratory activity is closely related to vascular activity. Consequently, the at least one vital parameter can represent the subject's heartbeat, heart rate, heart rate variability, respiration rate, respiration rate variability, pulse oxygen saturation, and suitable derivates and combinations thereof. In a preferred embodiment the processing unit can make use of photoplethysmographic or, even more preferred, remote photoplethysmographic approaches. Basically, circulatory activity of the subject can be monitored in a mediate way through observing the subject's skin. Slight fluctuations of skin appearance, such as skin color fluctuations, can be attributed to vascular activity, for example.

As used herein, each of the terms "indicative entities" and "non-indicative entities" may refer to particular signal fractions or elements (in terms of an observed area). It is worth noting that each of the indicative entities and the non-indicative entities may refer to at least a single area element or to a set of area elements. By way of example, given that the input signal is encoded in (digitized) data representative of vision-based information or image information, the respective entities may refer to at least a pixel or to a set of pixels. For instance, when a sequence of signal samples (or: image samples) is processed, each of the indicative entities and the non-indicative entities may be formed of respective portions in the samples. Assuming that the input signal is still embodied in form of electromagnetic radiation, the indicative entities and the non-indicative entities may refer to respective portions of the observed area. Also in this case both the indicative entities the non-indicative entities can be formed of a respective signal sub-portion or of a respective set of sub-portions.

The at least one defined descriptive model can be embodied by a model for (directly or indirectly) describing skin in terms of electromagnetic radiation. It is preferred in some embodiments that the descriptive model is a human skin representation model or, more specifically, a human skin color model.

According to a further aspect, the signal detector unit comprises at least one color filter element comprising a filter response adapted to spectral properties corresponding to the at least one descriptive model. The at least one filter element can be embodied by at least one optical filter. The at least one color filter element can also comprise a color filter array comprising a plurality of single filter elements. The at least one color filter element can be configured in such a way that basically indicative entities may pass the respective filter element while non-indicative entities are blocked, or at least, attenuated. It is preferred that the at least one filter element is configured for stopping non-indicative entities. By way of example, the at least one color filter element can comprise filter characteristics adapted to skin color properties. In this way, skin-indicative entities may pass while non-skin entities can be blocked, suppressed, or stopped.

The at least one color filter element can be formed by at least one optical lens filter, for example. In the alternative, the at least one color filter element can be embodied by at least one semiconductor optics filter element. By way of example, the at least one color filter element can be embodied by a Bayer filter array making use of a plurality of semiconductor filters. In this way, incoming signals can be filtered at the level of the sensor device before being converted into digital data. Therefore, no digital representation or, if at all, merely a manipulated representation of the non-indicative entities can be encoded or present in captured digital signals. In other words, the device can make use of a sensor means to which a respective input filter element is coupled which filters input radiation such that basically skin-indicative entities may pass, while non-skin entities are blocked, or, at least, attenuated.

According to yet another aspect the input signal comprises an input sequence of signal samples, wherein the signal detector unit comprises at least one data processing detector configured for processing respective signal samples of the input sequence under consideration of spectral information embedded in signal sample entities, thereby generating a transmitted signal sequence, wherein the at least one data processing detector is further configured for detecting the indicative entities under consideration of the at least one descriptive model describing a relation between physical appearance characteristics and a corresponding data representation in the signal samples.

This aspect can make use of digital data processing of an input sequence already captured and encoded (into digital data) in advance. A suitable analogue-digital converter can be formed by a respective sensor means, for instance, a camera. To this end, for instance, CCD-cameras and CMOS-cameras can be envisaged. Consequently, a basically discrete sequence of signal samples (or: frames) can be captured and delivered to the signal detector unit.

According to this aspect, each entity may comprise at least a single pixel or a set of pixels. It is worth mentioning in this connection that, by detecting or identifying indicative pixels in the signal samples, vice versa, also the non-indicative entities can be identified, at least in a mediate way. Consequently, each of the signal samples in the input sequence can be segmented into at least one indicative portion and at least one non-indicative portion. It is preferred that the at least one non-indicative portion (which indeed can be indicative of privacy information) is excluded from further signal processing or distribution measures.

The at least one descriptive model may provide a link between physical skin appearance characteristics in terms of electromagnetic radiation characteristics and a corresponding digital data representation making use of signal encoding conventions for visual signals in digital data.

According to yet another aspect the device may further comprise a masking unit configured for masking respective non-indicative entities in the transmitted signal sequence, wherein the data processing detector is further configured for classifying entities into one of an indicative state and a non-indicative state. For instance, the data processing detector can be configured to flag respective pixels in the signal samples. In this way, at least one of an indicative state and a non-indicative state can be assigned to respective pixels and, consequently, to respective entities. To this end, the data processing detector can make use of a skin classifier or, more particularly, of a skin pixel classifier.

Eventually, a transmitted signal can be obtained which is based on the input signal sequence and still comprises indicative entities or portions. On the contrary, the transmitted signal sequence may further comprise masked portions or entities which may replace non-indicative entities. By way of example, the masking unit can be configured for assigning a constant (color) value to non-indicative entities. Furthermore, according to an alternative aspect, the masking unit can be configured for blurring non-indicative pixels, or, more preferably, non-indicative portions comprising a plurality of non-indicative pixels. Typically, blurred portions may sufficiently hide underlying privacy-related information. As used herein, the term blurring may refer to various image manipulating measures directed at reducing (privacy) information content. It can be envisaged in this connection that further image or data manipulating measures can be applied to non-indicative portions of the signal samples so as to hide respective privacy information.

According to yet an even further aspect the signal samples are encoded under consideration of a signal space convention applying a color model, wherein an applied signal space comprises complementary channels for representing the entities forming the signal samples, wherein respective components of the entities are related to respective complementary channels of the signal space.

Typically, digital image representation requires an A/D (analogue/digital) conversion under consideration of a predefined conversion convention. In other words, the entities in the signal samples may comply with a signal space convention which basically describes a relation between electromagnetic radiation characteristics and respective signal properties of the entities in the (digital) signal samples. Typically, a signal space or color space may involve a combination of a color model and a respective mapping function which is utilized for data generation. Generally, the signal space may comprise two or more dimensions. A single pixel in a signal sample may be represented by a value or a respective vector (herein also referred to as index element) in the signal space.

In some embodiments, the signal space is an additive color signal space, wherein the complementary channels are additive color channels, wherein the entities are represented by at least three absolute components, wherein the at least three absolute components represent distinct color components indicated by the additive channels, and wherein the additive channels are related to define spectral portions. Such a color space may be embodied by an RGB color space, or by derivates thereof. Furthermore, subtractive color signals spaces can be envisaged, for instance, a CMYK color space, and respective derivates. Still, alternatively, the signal space can be configured as a signal space basically indicative of luminance information and chrominance information. This may apply, for instance, to the YUV color space.

According to a further aspect the signal space comprises a color representation basically independent of illumination variations. It should be noted in this connection, that also a "reduced" signal space may be utilized for detecting the indicative entities and, respectively, the non-indicative entities in the signal samples. By way of example, a subspace of the YUV signal space can be utilized to this end. Furthermore, signal spaces can be converted into derivative signal spaces in which luminance information is basically disregarded. By way of example, an additive color signal space (such as RGB) can be "mapped" to a chromaticity plane which may provide for color property representation regardless of actual luminance. In this way, luminance normalization can be achieved. Consequently, the detection of the indicative entities can be facilitated. For instance, respective R-values, G-values and B-values of the RGB signal space can be divided by a predefined linear combination of R, G and B, respectively. Such a normalization can further provide for a dimensional reduction. Preferably, the descriptive model or skin model makes use of the signal space in that an underlying vision-based skin model is defined and expressed in terms of the respective signal space convention.

According to another aspect it is further preferred that the descriptive model is a skin color model describing skin representation under consideration of signal space conventions. By way of example, the descriptive model can make use of look-up table data for comparison measurement and classification. The look-up table data may comprise a variety of predefined values representing indicative entities. According to one embodiment, the descriptive model is an explicit skin model. An explicit skin model may comprise a defined subspace of a signal space which is considered attributable to a representation of the subject's skin, for example. However, in the alternative, the descriptive model can be at least one of a non-parametric skin model and a parametric skin model.

By way of example, a non-parametric skin model can be based on a look-up table comprising a plurality of histograms representing a variety of reference measurements. A parametric skin model can make use of a simplified function-type representation of classification data in the signal space. By way of example, based on histograms obtained through reference measurements, Gaussian functions can be defined for describing a probability distribution with regard to whether or not a given entity (or: pixel) can be considered as an indicative entity or a non-indicative entity. In this connection, single Gaussian and multiple Gaussian functions can be envisaged.

According to another advantageous aspect, the masking unit is further configured for processing the indicative entities such that the at least one vital parameter is substantially detectable in the transmitted signal sequence, wherein non-indicative side information represented by the indicative entities is at least partially attenuated in the transmitted signal sequence. In this context, processing the indicative entities may involve blurring sets of indicative entities.

This embodiment is based on the idea that also the indicative entities can be processed so as to further enhance privacy preservation. It is preferred in this connection that processing parameters are chosen such that the to-be-extracted vital parameter is substantially preserved in the processed samples. Since vital parameter extraction may involve spatially averaging indicative regions of interest, blurring operations or similar algorithms can be applied to the indicative entities, provided that respective average values of interest (e.g., spatial mean pixel color values) remain substantially unchanged. By way of example, a blurring algorithm (e.g., Gaussian blur) can be applied to the indicative entities. In this way, privacy-related information, such as skin details, etc., can be diminished or attenuated while vital parameter-indicative information can be preserved, that is, for instance, a mean pixel color in an indicative region of interest is not affected. Consequently, mean pixel color fluctuations can be preserved for further analysis. By way of example, spatial blurring involving selective filter algorithms may be applied to the regions comprising the indicative entities.

It is further preferred in this connection that blurring parameters (e.g., blurring filter characteristics) are chosen such that indicative entities or sets of indicative entities comprising high contrast (huge differences in luminance and/or color) are excluded from blurring operations. High contrast areas may adversely influence average values and may therefore distort processed vital parameter-representative signals.

It is further envisaged to apply blurring operations or similar image processing operations to both the indicative entities and the non-indicative entities. In this connection, however, it is preferred that regions comprising the indicative entities and regions comprising the non-indicative entities are processed separately so as to avoid blending or mixing up indicative entities and non-indicative entities.

According to yet another aspect, the device further comprises a database providing a plurality of descriptive models attributable to an influence parameter selected from the group consisting of skin color type, ethnic region, ethnic group, body region, sex, sensor unit characteristics, and illumination conditions, and combinations thereof.

According to this approach the device can make use of a descriptive model currently considered suitable for an actual monitoring environment. The plurality of descriptive models may comprise a plurality of non-parametric skin models. In this case, even though non-parametric skin models can be considered somewhat inflexible or static, the device as a whole can be adapted to varying monitoring conditions.

According to an alternative exemplary aspect the signal detector unit is further configured for adapting the present descriptive model under consideration of an influenced parameter selected from the group consisting of skin color type, ethnic region, ethnic group, body region, sex, sensor unit characteristics, and illumination conditions, and combinations thereof. By way of example, a parameter of a parametric skin model can be adjusted accordingly so as to adapt the descriptive model to given monitoring conditions. It is worth mentioning in this connection that the above influence parameters basically may influence the appearance and the perception of skin colors and, therefore, may also influence accuracy of the indicative entity detection.

According to still yet a further aspect the device further comprises a sensor unit, in particular a camera, configured for sensing electromagnetic radiation at a distance, wherein the sensor unit is coupled to the signal detector unit such that non-indicative entities in the input signal are basically disregarded when transmitting respective signal samples. By way of example, a camera can be integrated in the device such that no external excess to a captured input sequence is allowed.

According to yet another aspect the sensor unit comprises a response characteristic adapted to the descriptive model such that non-indicative entities are basically disregarded when capturing the signal samples. In this connection, the detector unit and the masking unit can be implemented in the camera, for instance, via optical components, (digital) data processing components, and combinations thereof.

According to yet another aspect the device may further comprise an output interface for distributing the sequence of processed samples. The sequence of processed samples in which non-indicative entities are basically undetectable can be forwarded, distributed or copied without the risk of revealing non-indicative side information.

According to a further aspect the device further comprises a feature detector configured for detecting identity-related prominent features in signal samples of the input sequence, and a feature masking unit configured for masking respective entities in the transmitted signal sequence. This embodiment may even further contribute in enhancing privacy preservation. By way of example, the feature detector can be configured for applying eye recognition, face recognition, mouth recognition, hair recognition, and combinations thereof. Since primarily skin portions in the subject of interest are addressed, additional prominent features which may be considered even further indicative of privacy-related information (rather than of vital parameters of interest) can be detected and removed from the respective signal sample.

According to yet an even further aspect the processing unit is further configured as photoplethysmographic processing unit capable of extracting the at least one vital parameter of interest from the sequence of transmitted samples, wherein the at least one vital parameter can be extracted under consideration of vascular activity represented by skin color properties.

There exist several embodiments of the signal detector unit and the processing unit and, if any, of respective subcomponents thereof. In a first, fairly simple embodiment the signal detector unit and the processing unit as well as their respective (data processing) subcomponents can be embodied by a common processing device which is driven (or: controlled) by respective logic commands Such a processing device may also comprise suitable input and output interfaces. However, in the alternative, each of the signal detector unit and the processing unit can be embodied by separate processing devices controlled or controllable by respective commands. Hence, each respective processing device can be adapted to its special purpose. Consequently, a distribution of tasks can be applied, wherein distinct tasks are processed (or: executed) on a single processor of a multi-processor processing device or, wherein image processing related tasks are executed on an image processor while other operational tasks are executed on a central processing unit. The above may also refer to subcomponents of the signal detector unit and the processing unit. Each of the processing unit, the signal detector unit and their respective subcomponents can be implemented as a virtual part of a processing environment or as a discrete (e.g., hardware-coded) processing element. Hybrid implementations can be envisaged.

In a further aspect of the disclosure a method for processing data derivable from remotely detected electromagnetic radiation emitted or reflected by a subject is presented, the data comprising physiological information, the method comprising the steps of:

receiving an input signal and transmitting indicative entities thereof, the indicative entities being indicative of physiological information representative of at least one vital parameter in a subject of interest;

detecting the indicative entities under consideration of at least one defined descriptive model describing a relation between physical skin appearance characteristics and a corresponding representation in the input signal such that non-indicative side information represented by non-indicative entities in the input signal is substantially undetectable in a resulting transmitted signal; and extracting the at least one vital parameter from the transmitted signal comprising the indicative entities, wherein the at least one vital parameter is extracted under consideration of detected skin color properties representing circulatory activity.

Advantageously, the method can be carried out utilizing the device for extracting information of the disclosure.

In yet another aspect of the present disclosure, there is provided a computer readable non-transitory medium having instructions stored thereon which, when carried out on a computer, cause the computer to perform the steps of a method in accordance with the present disclosure. The program code (or: logic) can be encoded in one or more non-transitory, tangible media for execution by a computing machine, such as a computer. In some exemplary embodiments, the program code may be downloaded over a network to a persistent storage from another device or data processing system through computer readable signal media for use within the device. For instance, program code stored in a computer readable storage medium in a server data processing system may be downloaded over a network from the server to the device. The data processing device providing program code may be a server computer, a client computer, or some other device capable of storing and transmitting program code.

As used herein, the term "computer" stands for a large variety of processing devices. In other words, also mobile devices having a considerable computing capacity can be referred to as computing device, even though they provide less processing power resources than standard desktop computers. Furthermore, the term "a computer" may also refer to a distributed computing device which may involve or make use of computing capacity provided in a cloud environment.

Preferred embodiments of the invention are defined in the dependent claims. It should be understood that the claimed method and the claimed computer program can have similar preferred embodiments as the claimed device and as defined in the dependent device claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

The following section describes exemplary approaches to remote vital signal detection, in particular remote photoplethysmography (remote PPG), utilizing several aspects of the device and method in accordance with the present disclosure. It should be understood that single steps and features of the shown approaches can be extracted from the context of the respective overall approach. These steps and features can be therefore part of separate embodiments still covered by the scope of the invention.

Basic approaches to remote photoplethysmography are described in Verkruysse, W. et al. (2008), "Remote plethysmographic imaging using ambient light" in Optics Express, Optical Society of America, Washington, D.C., USA, Vol. 16, No. 26, pages 21434-21445. WO 2011/042858 A1 (US 2012/0195473) discloses a further method and system addressing processing a signal including at least one component representative of a periodic phenomenon in a living being.

In these and similar measurements often images or image-like representations of monitored subjects are captured. Typically, also the image background which is not indicative of the vital parameters of interest is still present in the captured data. Consequently side information which may allow conclusions regarding the subject's privacy can still be extracted from the recorded data. As used herein, the term "side information" typically refers to information which is not indicative of the vital parameters of interest but which may still contain privacy-related information.

Figure 1:
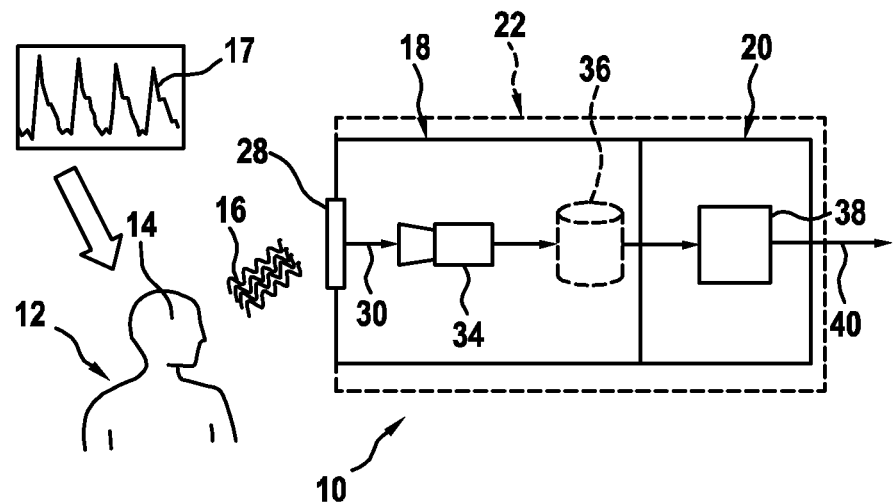
FIG. 1 shows a schematic illustration of a first general layout of a device according to the present disclosure.

FIG. 1 is referred to showing a schematic illustration of a device for processing data in a vital signal detection environment. The device is denoted by a reference numeral 10. For instance, the device 10 can be utilized for processing image frames representing a remote subject 12 for remote PPG monitoring. Typically, regions of interest 14 in the subject 12 are targeted. At least one region of interest 14 can be present in a recorded frame. Typically, the region of interest 14 may represent a face portion or, more generally, a skin portion of the subject 12. By way of example, in case the subject 12 wears a T-shirt three regions of interest 14 can be present in a captured frame, namely a head or face portion and two respective forearm portions. Needless to say, a recorded frame may also comprise a representation of more than one subject 12. Typically, the captured data can be derived from electromagnetic radiation 16 basically emitted or reflected by the subject 12. When processing the recorded signals, eventually a vital parameter 17 of interest can be derived from the electromagnetic radiation 16. The vital parameter 17 may relate to a vital signal attributable to the subject's 12 vascular or respiratory activity.

The device 10 comprises a signal detector unit 18 and a signal processing unit 20. Both the signal detector unit 18 and the signal processing unit 20 can be implemented in a common housing 22. The housing 22 may also stand for a system boundary. Within the system boundary, both the signal detector unit 18 and the processing unit 20 can be arranged discretely. Furthermore, both the signal detector unit 18 and the processing unit 20 can be implemented as a (single) common integral part of the device 10.

The device 10 illustrated in FIG. 1 can make use of at least one upstream color filter element 28. The at least one upstream color filter element 28 can be placed in front of at least one sensing element of a sensor unit 34. Consequently, the at least one color filter element 28 can be configured for receiving an input signal (directly) from the incident electromagnetic radiation 16 and transmitting a transmitted signal 30 to the sensor unit 34. In other words, the at least one color filter element 28 can be configured for directly processing electromagnetic radiation rather than processing a digital data representation of electromagnetic radiation. The at least one color filter element 28 can comprise a respective optical filter element. In some cases, the optical filter element can be embodied by an optical lens. Furthermore, a set of suitably arranged optical lenses can be envisaged. However, in the alternative, or in addition, the at least one color filter element 28 can also be embodied by at least one semiconductor filter element. Such a filter element can be part of a Bayer filter element of, more preferably, of a Bayer filter array. Needless to say, the at least one color filter element 28 can be (physically) directly attached to the sensor unit 34.

In connection with the device 10 elucidated in FIG. 1 it is preferred that the at least one color filter element 28 implements the at least one descriptive model, for instance, the descriptive skin color model. That is, the at least one color filter element 28 preferably comprises a filter response which may be adapted to assumed skin representation characteristics in electromagnetic radiation. Consequently, non-indicative side information (non-skin entities) in the input signal can be blocked or, at least, attenuated before being captured by the sensor unit 34.

The sensor unit 34 can be embodied by a digital camera configured for recorded imaging frames. Such a camera can make use of CCD sensors or CMOS sensors, for example. In this way, the sensor unit 34 can implement an analogue-digital conversion of the input signals. The converted (digitized) data can be delivered to an (optional) data buffer or storage 36. The data storage 36 may serve as a short-term cache or as a long-term memory. It should be understood that the data storage 36 can form part of the signal detector unit 18 or of the processing unit 20. Furthermore, each of the signal detector unit 18 and the processing unit 20 may comprise at least one data storage. Additionally, the data storage 36 can be interposed between the signal detector unit 18 and the processing unit 20, refer to FIG. 3.

In FIG. 1, the processing unit 20 can receive the processed signals in which indicative information is still embedded, while non-indicative information is basically undetectable. It is worth mentioning again in this connection that the terms "indicative" and "non-indicative" have to be interpreted in terms of the detection of the desired vital parameters 17 of interest. By way of example, the processing unit 20 may comprise a signal extractor 38 which may be configured for applying PPG signal extraction algorithms. Consequently, a processed signal 40 can be generated and distributed which may represent the vital parameter 17 or, at least, indicative signal entities which are highly indicative of the vital parameter 17. The arrangement shown in FIG. 1 can be considered as a privacy preserving arrangement since even though a sensor unit 34 is utilized which is basically capable of capturing indicative signal entities and non-indicative signal entities, no digital data comprising both the indicative entities and a plain representation of the non-indicative entities is accessible from the outside of the system boundary 22 of the device 10.

Figure 2:
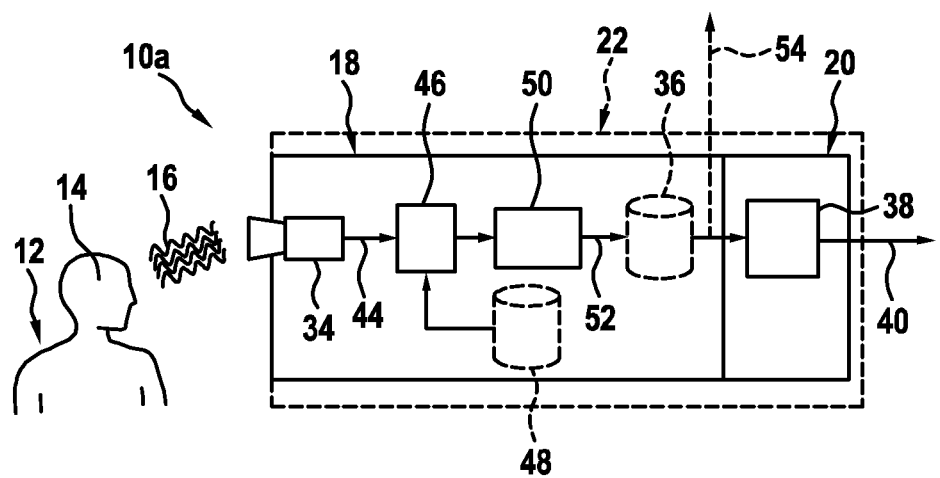
FIG. 2 shows a schematic illustration of an alternative layout of a device according to the present disclosure.

In FIG. 2, a similar device 10a is presented which basically makes use of privacy preservation measures applicable to digitized image information, that is, to signals downstream of the sensor unit 34. In this embodiment, the sensor unit 34 can be basically capable of sensing a whole portion of the electromagnetic radiation 16 (e.g., the whole visible radiation portion) which may comprise both the indicative entities and the non-indicative entities. In this way, an input sequence 44 can be generated. Typically, the input sequence 44 comprises digitized data. The input sequence 44 may comprise a series of frames, more particularly, a series of image frames. The input sequence 44 can be delivered to a processing detector 46. The processing detector 46 can be configured for processing frames (herein also referred to as samples) of the input sequence 44. Typically, the processing detector 46 can seek for indicative entities in the signal samples. This can be performed under consideration of at least one descriptive model. In FIG. 2, digitized data is processed by the processing detector 46. Therefore, the at least one descriptive model may describe a relation between physical appearance characteristics of indicative entities and a corresponding data representation in the (digitized) signal samples.

By way of example, the signal detector unit 18 may further comprise a database 48 for storing and providing the at least one descriptive model. However, in the alternative, the processing detector 46 can also implement the at least one descriptive model which may be encoded in hardware or in software in the processing detector 46. In some embodiments, in particular when the processing detector 46 is configured for comparative detection of the indicative entities, the database 48 may comprise look-up comparison data for classifying entities (that is, single pixels or sets of pixels) in the signal samples. In some embodiments, the processing detector 46 can be configured to "flag" the entities in the signal samples according to their classified state.

Further, downstream in the signal detector unit 18 a masking unit 50 may be provided which can be configured for masking detected non-indicative entities. As mentioned above, the detection of the non-indicative entities can be carried out in a mediate way in that primarily indicative entities are detected. Consequently, remaining entities not classified as indicative entities can be classified as non-indicative entities. By way of example, the masking unit 50 can be configured for replacing the non-indicative entities in the signal samples by replacement entities having a constant color or value. Furthermore, alternatively, the masking unit 50 can be configured for blurring the non-indicative entities. A blurring operation or a similar image processing operation is preferably applied to a considerably large portion of the signal samples. In other words, preferably blurring operations are applied to entities or sets of entities comprising a plurality of pixels.

In some embodiments, alternatively, or in addition, the masking unit 50 can be further configured for blurring the indicative entities. It is also preferred in this connection that considerably large (indicative) portions of the signal samples are blurred. Preferably, the masking unit 50 is capable of reducing non-indicative privacy information in the indicative entities while still allowing the vital parameter of interest 17 to be extracted therefrom. It should be noted in this context that a blurring operation should be separately applied to the indicative entities and to the non-indicative entities so as to avoid mixing up the respective regions and the information embedded therein.

Upon detecting and masking non-indicative entities in the signal samples, a transmitted sequence 52 can be generated in which non-indicative side information is basically undetectable. The transmitted sequence 52 can correspond to the input sequence 44 with respect to frame rate and frame size (resolution). Eventually, the transmitted sequence 52 can be delivered to the (optional) data storage 36 and, consequently, to the signal extractor 38 in the processing unit 20 for vital parameter extraction measures. It is preferred that the device 10*a* is arranged in such a way that no external access to the (unprocessed) input sequence 44 is allowed. In case it is intended to distribute a sequence of signal samples without revealing unnecessary privacy information, the device 10*a* may provide for an external access to the transmitted sequence 52, refer to the reference numeral 54.

Figure 3:
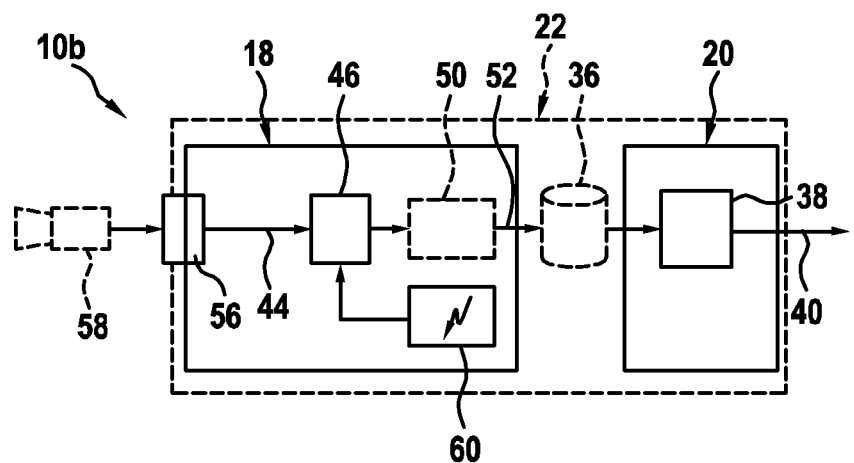
FIG. 3 shows yet another schematic illustration of an alternative layout of a device according to the present disclosure.

FIG. 3 illustrates a further alternative embodiment of a device for processing data and extracting physiological information which is denoted by a reference numeral 10*b*. The device 10*b* is configured for cooperating with an external sensor unit 58. The sensor unit 58 can be arranged separate (or: distant) from the device 10*b*. The external sensor unit 58 can be configured for capturing an input sequence which may be delivered to an interface 56. It should be understood that the external sensor unit 58 can be used for capturing the image sequence in advance. Consequently, the device 10*b* can also be configured for processing an input sequence 44 which has been stored for buffered. Still, however, in some cases recording and processing the input sequence 44 can be performed basically simultaneously. Input data can be delivered from the external sensor unit 58 to the interface 56 via suitable cable or wireless connections. It can be also envisaged that an external data storage (not shown in FIG. 3) can be coupled to the interface 56 for delivering previously collected data.

In FIG. 3, the signal detector unit 18 does not necessarily have to comprise an (internal) sensor unit. Instead, the input sequence 44 can be delivered through the interface 56 to the data processing detector 46. An (optional) masking unit 50 may also be provided in the signal detector unit 18 in FIG. 3. The masking unit 50 can be considered optional since basically also the processing detector unit can be configured for masking or blocking respective non-indicative entities in the samples of the input sequence 44 by itself. The signal detector unit 18 may further comprise a detector adaptor element 60. The detector adaptor element 60 can be utilized in connection with a descriptive model which is configured as a parametric skin model. Consequently, the detector adaptor element 60 can be configured for suitably adjusting parameters of the descriptive model. In particular a parametric skin model may comprise parameters which can be adjusted according to changes in influence parameters. An influence parameter can be selected from the group consisting of skin color type, ethnic region, ethnic group, body region, sex, sensor unit characteristics, and illumination conditions, and combinations thereof. Consequently, either via manual operations or via automatic (calibration) operations, a respective influence parameter variation can be detected and, consequently, the parametric skin model can be adjusted accordingly. Eventually, a transmitted sequence 52 can be delivered to a respective processing unit 20, either directly or indirectly via an (optional) data storage 36.

Figure 4A:
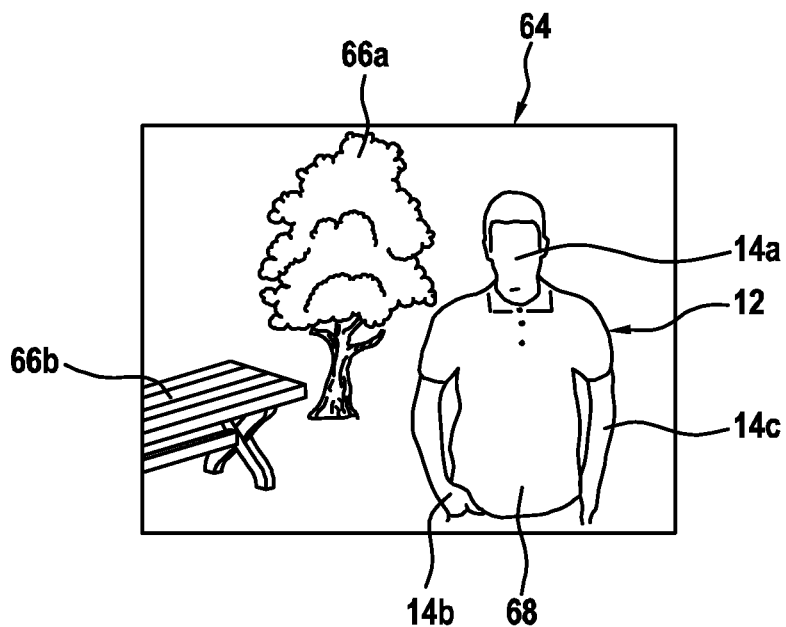
FIGS. 4a, 4b show an exemplary input signal sample comprising indicative entities and non-indicative entities; and a respective (processed) transmitted signal sample in which the non-indicative entities are substantially undetectable.
Figure 4B:
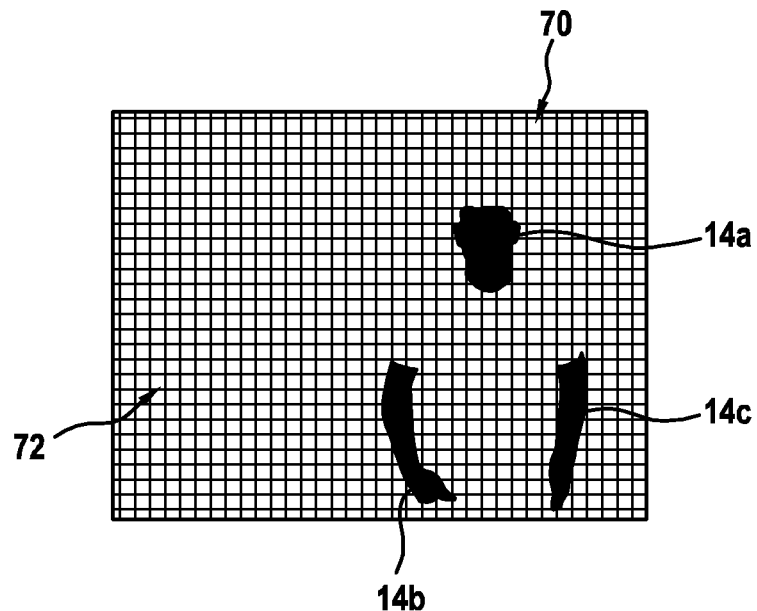

FIG. 4*a* and FIG. 4*b* exemplarily illustrate an input signal sample 64 and a corresponding (processed) transmitted signal sample 70. The signal sample 64 comprises a representation of a subject of interest 12 exposing several regions of interest 14*a*, 14*b*, 14*c* which can be considered indicative of an underlying vital parameter. Furthermore, non-indicative regions 68 in the subject 12 are present. For instance, the non-indicative region 68 can be formed by a body region covered in cloths. Furthermore, the input signal sample 64 can be indicative of surrounding elements 66*a*, 66*b* which are also considered non-indicative of the desired vital parameters. Typically, merely the regions of interest 14*a*, 14*b*, 14*c* are required for the desired signal extraction. On the contrary, the surrounding elements 66*a*, 66*b* and the non-indicative region 68 or, more generally, the background of the signal sample 64, may comprise privacy-related information allowing conclusions with regard to the housing situation, the current location, the wealth status, or even the personality of the subject 12. It is therefore desirable that such add-on information (herein also referred to as side information) can be excluded from any circulation or transmission of the respective data.

The transmitted signal sample 70 shown in FIG. 4*b* can form a part of the transmitted sequence generated in the signal detector unit 18 upon processing the input sequence 44 (refer to FIGS. 2 and 3). On the contrary, the signal sample 64 shown in FIG. 4*a* can form a respective part of the input sequence 44. As indicated above, in the transmitted signal sample 70 basically the regions of interest 14*a*, 14*b*, 14*c* comprising the indicative entities are preserved while side information is removed from or suppressed in the transmitted signal sample 70. Consequently, a region 72 is formed in the transmitted signal sample 70 which may basically be considered as a masked region, or a region of blanks or constant values. It is worth mentioning in this connection that the signal entities representing the regions of interest 14*a*, 14*b*, 14*c* in FIG. 4*b* may basically correspond to or have the same values as the respective entities in FIG. 4*a*. Merely for illustrative purposes, the regions 14*a*, 14*b*, 14*c* are blackened in FIG. 4*b*. Correspondingly, also the squared pattern of the region 72 has been added for illustrative purposes. It follows from FIG. 4*b* that the transmitted signal sample 70 indeed addresses privacy protection measures in that unnecessary privacy-related information is no longer present.

Figure 5:
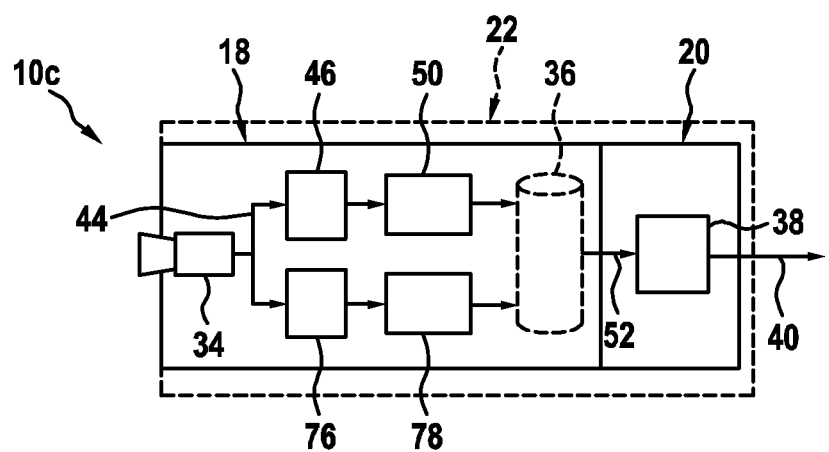
FIG. 5 shows a schematic illustration of yet an even further alternative layout of a device according to the present disclosure.

FIG. 5 exemplarily illustrates a general layout of another alternative device for processing data and for extracting physiological information. The device 10*c* may have a similar layout as the device 10*a* illustrated in FIG. 2. The signal detector unit 18 of the device 10*c* further comprises a feature detector 76 and a corresponding feature masking unit 78. The feature detector 76 and the feature masking unit 78 can further contribute in privacy protection. To this end, the feature detector 76 can be configured for detecting prominent features in the subject 12 which is monitored for vital parameter extraction purposes. Feature detection can make use of descriptive feature models describing a representation of prominent features in potentially indicative regions of interest in the subject 12.

Figure 6A:
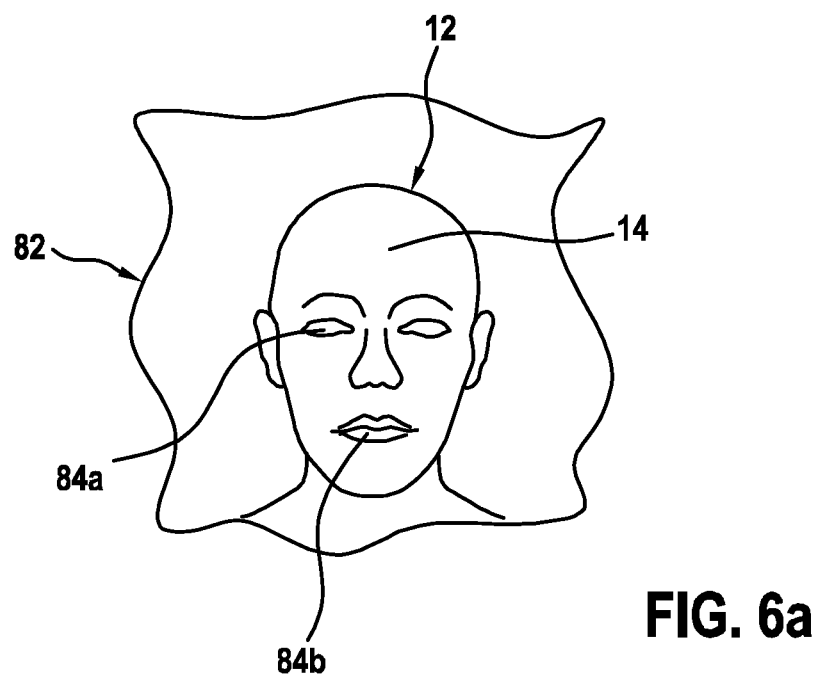
FIGS. 6a, 6b show a signal sample section illustrating a subject of interest; and a respective section of a (processed) transmitted signal sample in which prominent features in the subject are masked.
Figure 6B:
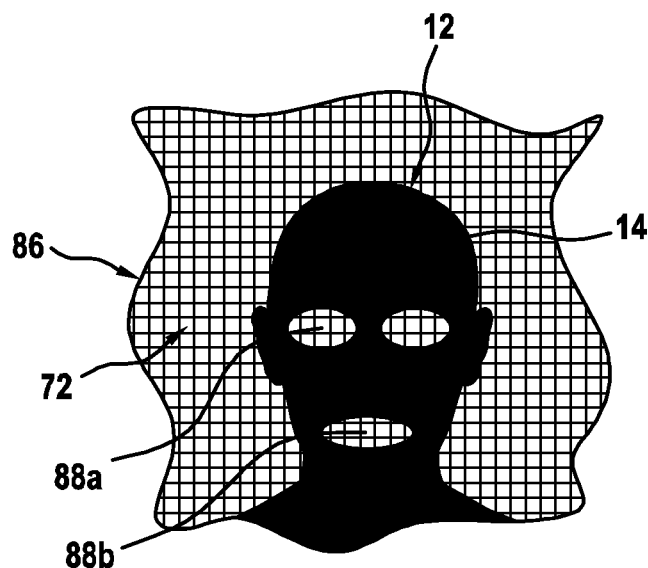

In this connection, further reference is made to FIG. 6*a* and FIG. 6*b*. Both FIG. 6*a* and FIG. 6*b* show corresponding sections of a signal sample representing a subject 12. FIG. 6*a* shows a section 82 taken from an input signal sample. FIG. 6*b* shows a corresponding section 86 taking from a transmitted sample. Feature detection can be directed at prominent features which can be considered identity-related features. For instance, features 84a (eye region) and 84b (mouth region) in FIG. 6b can be considered identity-related features. Advantageously, for further enhancing a privacy protection level, these features 84a, 84b can be detected and masked or blocked such that they are substantially undetectable in the respective transmitted sample. The corresponding section 86 in FIG. 6b comprises a representation of the region of interest 14 which is considered highly indicative of the vital parameter of interest, while also a masked region (or: region of blanks) 72 is present. Furthermore, identity-related features are replaced by respective masked portions 88a, 88b which basically allow no conclusions regarding the personality of the subject of interest 12.

The feature detector 76 shown in FIG. 5 can be utilized for detecting the respective identity-related features 84a, 84b. The feature masking unit 78 which may alternatively also be integrated into the feature detector 76 may mask, suppress, or attenuate respective entities in the signal samples so as to arrive at a transmitted sample in which merely masked features 88a, 88b are present. As indicated in FIG. 5, the feature detector 76 and the feature masking unit 78 can be configured for processing the input (sample) sequence 44 in parallel with the data processing detector 46 and the respective masking unit 50. However, according to an alternative approach, the feature detector 76 and the feature masking unit 78 can also be configured for processing signal samples which have been preprocessed by the data processing detector 46 and the masking unit 50. Still, also alternative processing orders can be envisaged.

Figure 7:
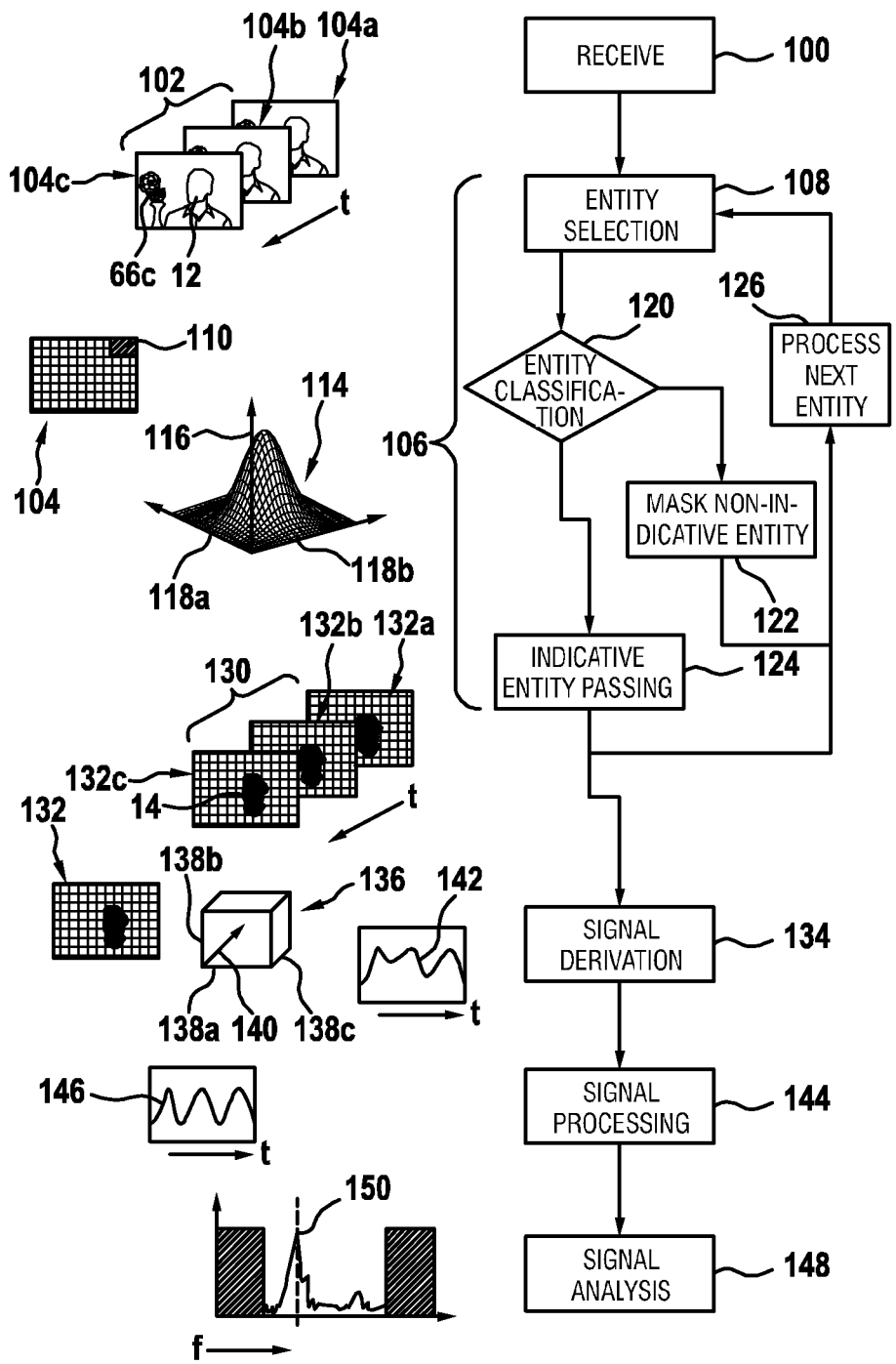
FIG. 7 shows an illustrative block diagram representing several steps of an embodiment of a method in accordance with the disclosure.

Having demonstrated several alternative exemplary approaches covered by the disclosure, FIG. 7 is referred to, schematically illustrating a method for processing data and for extracting physiological information.

Initially, in a step 100, an input data stream or an input sequence 102 of signal samples 104a, 104b, 104c is received. A time-axis is indicated by an arrow t. Each of the signal samples 104a, 104b, 104c may comprise a representation of a subject 12 of interest, and of surrounding elements 66c, or, more generally, background information or side information.

A subroutine 106 may follow which is basically directed at detecting indicative entities in the signal samples 104a, 104b, 104c and, consequently, at detecting also non-indicative entities. More specifically, the subroutine 106 can be directed at detecting skin portions and non-skin portions in the signal samples 104a, 104b, 104c. In a step 108 to-be-processed entities 110 in a signal sample 104 can be selected. As indicated above, the term "entity" may stand for single pixels or a set of pixels in the signal sample 104. In a subsequent classifying step 120 the respective entity 110 is classified into at least one of an indicative state and a non-indicative state. To this end, the classifying step 120 can make use of a descriptive model 114, in particular a descriptive skin model. The descriptive model 114 can comprise estimated characteristics of a representation of indicative entities in the signal samples 104.

By way of example, for illustrative purposes, the descriptive model 114 can comprise a probability distribution or a similar function graph or function surface. The descriptive model 114 can also make use of a set of (reference) histograms. In FIG. 7 the descriptive model 114 can be based on a probability distribution such as a Gaussian distribution for an input variable e.g., a respective to-be-classified signal entity 110. The variable can be characterized by respective values in a domain formed by at least one signal channel 118a, 118b. By way of example, two or even more signal channels can be utilized each of which may represent respective characteristics of electromagnetic radiation. Basically, a given variable may take any value within such a domain. Since the descriptive model 114 may provide for a variability distribution (refer to a probability axis 116), a classification as to whether the variable is considered indicative or non-indicative can be performed. As already indicated above, other types of descriptive models can be utilized. Therefore, the representation of the descriptive model 114 in FIG. 7 is merely provided for illustrative purposes.

Depending on the classification outcome a step 122 or a step 124 may follow. In the step 122 which may follow when the entity 110 is classified as non-indicative, the respective entity can be masked, blocked, attenuated or processed in a similar way so as to ensure that the non-indicative entity is basically undetectable in further signal operation stages. In the step 124 which may follow in case the respective entity 110 is classified as an indicative entity, the entity can be basically transmitted or allowed to pass. In this way, indicative entities are preserved in the data for further signal processing operations.

Regardless of the outcome of the classifying step 120 a further step 126 may follow which may be directed at creating a command that a next signal entity 110 has to be chosen and classified unless every single entity of the currently to-be-processed sample 104 has been classified. The respective command can be transferred to the entity selection step 108. In this way, the subroutine 106 can operate loop-wise.

Having accomplished the subroutine 106, eventually a transmitted sequence 130 of transmitted samples 132a, 132b, 132c can be generated in which primarily at least one indicative region of interest 14 is preserved. Side-information which is not necessary for vital parameter extraction measures is no longer detectable in the transmitted sequence 130. In a subsequent signal derivation step 134 a characteristic signal 132 can be derived from the transmitted sequence 130. To this end, the respective transmitted samples 132 can be processed so as to derive single values or index elements 140 on which the characteristic signal 142 is based. By way of example, the single value or index element 140 can represent mean characteristics of the region of interest 14 in the transmitted sample 132. Consequently, the single value or index element 140 can represent respective mean color characteristics. To this end, a vectorial representation of the index element 140 can be utilized.

The index element 140 can represent a certain value within a signal space 136, for instance, in a color space. The signal space 136 can be regarded as a convention for representing electromagnetic radiation characteristics in (digital) data. The signal space 136 may comprise several complementary channels 138a, 138b, 138c. In an exemplary non-limiting example an RBG color space can be envisaged. In this connection, the complementary channels 138a, 138b, 138c may represent respective R-, G-, and B-channels. In combination the complementary channels 138a, 138b, 138c form the signal space 136 and therefore a domain of values the index element 140 may take. By processing a plurality of transmitted samples 132 eventually a corresponding plurality of single values or index elements 140 can be obtained which form a basis for the characteristic signal 142. Typically, the characteristic signal 142 may represent slight (color) fluctuations in the region of interest 14.

In a further subsequent signal processing step 144 signal optimization and signal enhancement measures can be applied to the characteristic signal 142 so as to arrive at an enhanced characteristic signal 146. In this connection, several signal processing measures can be envisaged, including filtering, windowing, etc. In an additional signal extraction or signal analization step 148 a vital parameter, of interest 150 can be obtained. It should be understood that in some cases basically a time-based representation and/or a frequency-based representation of the vital parameter 150 might be of interest.

By way of example, the present disclosure can be applied in the field of healthcare, for instance, unobtrusive remote patient monitoring, in the field of general surveillances, e.g., security monitoring, and in so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. Needless to say, in an embodiment of the method in accordance with the disclosure, several of the steps described herein can be carried out in changed order, or even concurrently. Further, some of the steps could be skipped as well without departing from the scope of the disclosure. This applies in particular to several alternative signal processing steps. Several of the disclosed illustrative embodiments can take the form of hardware embodiments, software embodiments, or of embodiments containing both hardware and software elements. Some embodiments are implemented in software which may include firmware and application software.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible device or apparatus that can contain, store, communicate, propagate, or transport the program for use by or in connection with the instruction execution device.

In so far as embodiments of the disclosure have been described as being implemented, at least in part, by software-controlled data processing devices, it will be appreciated that the non-transitory machine-readable medium carrying such software, such as an optical disk, a magnetic disk, semiconductor memory or the like, is also considered to represent an embodiment of the present disclosure.

The computer usable or computer readable medium can be, for example, without limitation, an electronic, magnetic, optical, electromagnetic, infrared, or semiconductor system, or a propagation medium. Non-limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk—read only memory (CD-ROM), compact disk—read/write (CD-R/W), and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example, without limitation, physical or wireless.

A data processing system or device suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories, which provide temporary storage of at least some computer readable or computer usable program code to reduce the number of times code may be retrieved from bulk storage during execution of the code.

Input/output, or I/O devices, can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems, remote printers, or storage devices through intervening private or public networks. Non-limiting examples are modems and network adapters and are just a few of the currently available types of communications adapters.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A device for processing data derivable from remotely detected electromagnetic radiation emitted or reflected by a subject, the data comprising physiological information, comprising:
   a signal detector processor configured to:
      receive an input signal including indicative entities indicative of physical skin appearance characteristics representing circulatory activity representative of at least one vital parameter in a subject of interest,
      remove or mask the non-indicative entities to render the non-indicative entities undetectable,
      transmit a transmitted signal including the indicative entities and with the non-indicative entities removed or undetectable; and
   a wellness processor configured to:
      extract at least one vital parameter from the indicative entities of the transmitted signal based on the physical skin appearance characteristics.

2. The device as claimed in claim 1, further including a camera and at least one color filter element comprising a filter response adapted to spectral properties corresponding to at least one descriptive model configured to generate the received input signal.

3. The device as claimed in claim 1, wherein the input signal comprises an input sequence of signal samples, wherein the signal detector processor is further configured to process respective signal samples of the input sequence under consideration of spectral information embedded in signal samples to generate the transmitted signal.

4. The device as claimed in claim 3, wherein the input signal depicts a face of the subject and the detector processor is further configured to mask or remove entities representing eyes and a mouth of the subject.

5. The device as claimed in claim 3, wherein the signal detector processor is further configured to mask or remove entities indicative of wealth or status of the subject.

6. The device as claimed in claim 3, wherein the transmitted signal includes signal samples encoded under consideration of a signal space convention applying a color model, wherein an applied signal space comprises complementary channels for representing the entities forming the signal samples, wherein respective components of the entities are related to respective complementary channels of the signal space.

7. The device as claimed in claim 6, wherein the signal space comprises a color representation basically independent of illumination variations.

8. The device as claimed in claim 1, further comprising a database providing a plurality of descriptive models attributable to an influence parameter selected from the group consisting of skin color type, ethnic region, ethnic group, body region, sex, sensor unit characteristics, and illumination conditions, and combinations thereof.

9. The device as claimed in claim 1, wherein the signal detection processor is further configured to detect identity-related prominent features in signal samples of the input signal, and mask respective entities in the transmitted signal.

10. A device for processing data derivable from remotely detected electromagnetic radiation emitted or reflected by a subject, the data comprising physiological information, comprising:
a signal detector unit configured for receiving an input signal including an input sequence of signal samples, the signal detector unit including at least one data processor detector configured for processing respective signal samples of the input sequence under consideration of spectral information embedded in signal sample entities to generate a transmitted signal sequence and configured for classifying entities into one of an indicative state and a non-indicative state;
a masking unit configured for masking respective non-indicative entities in the transmitted signal sequence and configured for processing the indicative entities such that the at least one vital parameter is substantially detectable in the transmitted signal sequence, wherein non-indicative side information represented by the indicative entities is at least partially attenuated in the transmitted signal sequence, wherein the masking unit is further configured for blurring sets of indicative entities in the signal samples, wherein average characteristics of the indicative entities remain substantially unchanged, such that the at least one vital parameter of interest is substantially preserved in the transmitted signal sequence;
a processing unit configured for extracting at least one vital parameter from a transmitted signal sequence comprising the indicative entities;
wherein the indicative entities are indicative of physiological information representative of the at least one vital parameter in a subject of interest;
wherein the at least one vital parameter is extracted under consideration of detected skin color properties representing circulatory activity; and
wherein the signal detector unit is further configured for detecting the indicative entities under consideration of at least one defined descriptive model describing a relation between physical skin appearance characteristics and a corresponding representation in the input signal such that non-indicative side information represented by non-indicative entities in the input signal is substantially undetectable in the resulting transmitted signal.

11. A device for processing data derivable from remotely detected electromagnetic radiation emitted or reflected by a subject, the data comprising physiological information, comprising:
a signal detector means configured for receiving an input signal and for transmitting indicative entities thereof, the indicative entities being indicative of physiological information representative of at least one vital parameter in a subject of interest; and
a processing means for extracting the at least one vital parameter from a transmitted signal comprising the indicative entities;
wherein the at least one vital parameter is extracted under consideration of detected skin color properties representing circulatory activity;
wherein the input signal comprises an input sequence of signal samples;
wherein the signal detector means comprises at least one data processing detector means configured for processing respective signal samples of the input sequence under consideration of spectral information embedded in signal sample entities, thereby generating a transmitted signal sequence;
wherein the signal detector means is further configured for detecting the indicative entities under consideration of at least one defined descriptive model describing a relation between physical skin appearance characteristics and a corresponding representation in the input signal such that non-indicative side information represented by non-indicative entities in the input signal is substantially undetectable in the resulting transmitted signal;
a masking means for masking respective non-indicative entities in the transmitted signal sequence;
wherein the data processing detector means is further configured for classifying entities into one of an indicative state and a non-indicative state; and
wherein the masking means is further configured for processing the indicative entities such that the at least one vital parameter is substantially detectable in the transmitted signal sequence and that non-indicative side information represented by the indicative entities is at least partially attenuated in the transmitted signal sequence.

12. The device as claimed in claim 11, wherein the input signal is indicative of skin areas of the subject and wherein the masking means is further configured to mask subject identifying physical features of the subject.

13. The device as claimed in claim 11, wherein the input signal is indicative of a face of the subject and the masking means is further configured to mask at least one of lips and eyes.

14. The device as claimed in claim 11, wherein the masking means is further configured to mask indications of wealth and status of the subject.

15. The device as claimed in claim 11, wherein the entities indicative of identity include eyes, and further including masking the eyes in the transmitted signal.

16. The device as claimed in claim 11, wherein the entities indicative of identity include lips, and further including masking the lips in the transmitted signal.

17. A method for processing data derivable from remotely detected electromagnetic radiation emitted or reflected by a subject, the data comprising physiological information, comprising the steps of:
- receiving an input signal and transmitting indicative entities thereof, the indicative entities being indicative of physiological information representative of at least one vital parameter in a subject of interest;
- detecting the indicative entities under consideration of at least one defined descriptive model describing a relation between physical skin appearance characteristics and a corresponding representation in the input signal;
- masking non-indicative side information represented by non-indicative entities in the input signal and entities indicative of an identity, wealth, or status of the subject such that the non-indicative side information, identity, wealth, and status of the subject are substantially undetectable in a resulting transmitted signal; and
- extracting the at least one vital parameter from the transmitted signal comprising the indicative entities, wherein the at least one vital parameter is extracted under consideration of detected skin color properties representing circulatory activity.

18. The method as claimed in claim 17, wherein the input signal comprises an input sequence of signal samples, and wherein detecting the indicative entities comprises:
- processing respective signal samples of the input sequence under consideration of spectral information embedded in signal sample entities, thereby generating a transmitted signal sequence; and
- detecting the indicative entities under consideration of the at least one descriptive model describing a relation between physical appearance characteristics and a corresponding data representation in the signal samples.

19. A non-transitory computer readable medium having instructions stored thereon which, when carried out on a computer, cause the computer to perform the steps of the method as claimed in claim 17.

* * * * *